United States Patent [19]

Corbett et al.

[11] Patent Number: 4,915,935

[45] Date of Patent: Apr. 10, 1990

[54] PROCESS FOR APPLYING REFLECTIVE PARTICLES TO HAIR

[75] Inventors: John F. Corbett, Norwalk; Girish V. Patel, Bridgeport, both of Conn.

[73] Assignee: Clairol Incorporated, New York, N.Y.

[21] Appl. No.: 211,076

[22] Filed: Jun. 21, 1988

Related U.S. Application Data

[63] Continuation of Ser. No. 869,850, May 27, 1986, abandoned, which is a continuation of Ser. No. 685,203, Dec. 24, 1984, abandoned, and Ser. No. 639,169, Aug. 9, 1984, abandoned.

[51] Int. Cl.$^4$ .......................... A61K 7/06; A61K 7/07; A61K 7/11; A61K 9/12
[52] U.S. Cl. ............................ 424/47; 424/DIG. 1; 424/70; 514/945
[58] Field of Search .................................. 424/47, 70

[56] References Cited

U.S. PATENT DOCUMENTS

3,092,555  6/1963  Horn ....................... 424/70

FOREIGN PATENT DOCUMENTS

| | | | |
|---|---|---|---|
| 2064591 | 7/1971 | Fed. Rep. of Germany | 424/47 |
| 58-124713 | 7/1983 | Japan | 424/47 |
| 0008573 | 5/1907 | United Kingdom | 424/69 |
| 721045 | 12/1954 | United Kingdom | 424/70 |
| 2149806A | 6/1985 | United Kingdom | 424/47 |

OTHER PUBLICATIONS

Ash, *A Formulary of Cosmetic Preparations*, pp. 99–105 (1977).
Harry, *Cosmetic Materials*, vol. 2, pp. 129–131 (1963).

*Primary Examiner*—Dale R. Ore
*Attorney, Agent, or Firm*—Sandra M. Nolan

[57] ABSTRACT

A composition of matter for depositing reflective particles on hair, said composition comprising solid reflective particles dispersed in a moderately fast-breaking foam, said foam being suitable for application to the hair.

11 Claims, No Drawings

PROCESS FOR APPLYING REFLECTIVE PARTICLES TO HAIR

This is a continuation of U.S. Application Ser. No. 869,850 filed May 27, 1986, now abandoned which was a continuation of Ser. No. 685,203, filed Dec. 24, 1984 and Ser. No. 639,169 filed Aug. 9, 1984, both now abandoned.

I. DESCRIPTION

This invention relates to a process for imparting temporary high fashion "glitter" to hair, and particularly to hair on the human head, and to compositions that are useful for this purpose.

It is known in the prior art that a desirable high fashion appearance can be created by the application of reflective particles to the hair. Such reflective particles can be metallic, non-metallic inorganic micas, bismuth oxychloride or organic materials such as guanines (fish scales).

It has been proposed to accomplish this effect by simply sprinkling the reflective particles on the hair. Products are also available, for the deposition of such particles on the hair, in the form of aerosol sprays in which the particles are dispersed in a non-viscous volatile liquid carrier for application in the form of a fine mist. Alternatively, similar suspensions of the reflective particles can be applied to the hair by means of a paint brush.

Additionally, products are available in which the reflective particles are dispersed in a viscous medium and are applied to the hair by means of a small spiral brush. Alternatively, the reflective particles can be dispersed in a waxy medium and applied to the hair in the form of a crayon.

Each of the aforesaid methods of application suffers from a variety of disadvantages. The powders and aerosol sprays, for example, are difficult to control and have a tendency to deposit the reflective particles on the skin of the face and ears and on the clothing, in addition to the hair. Additionally, the direct application of particles can fall from the hair onto the forehead and shoulders of the wearer.

Use of the small brush type of application is limited to deposition of the reflective particles on small areas unless considerable time is taken to apply to the whole coiffure. The mascara brush type application suffers from a similar disadvantage. Additionally, products for application with the small siral (mascara-type) brush and crayons leave a waxy deposit on the hair which detracts from the tactile qualities.

These several disadvantages can be overcome according to the present invention in which the reflective particles are dispersed in a non-viscous, moderately rapid drying medium contained in an aerosol container and dispensed in the form of a moderately fast-breaking foam. A ball of foam is applied to the hair and spread through the desired areas by use of the fingers, a brush, or a comb. In the preferred form of the invention, insoluble coloring agents, for example, insoluble pigments are incorporated in the aerosol product to impart color to the reflective particles that are deposited on the hair. In the preferred aspect of this invention, a water-soluble hair setting resin is also incorporated in the present aerosol composition which will serve both as a styling aid and fixative to help retain the reflective particles on the hair.

It is accordingly an object of the present invention to provide an improved composition for imparting temporary high fashion glitter to hair, and particularly, hair on the human head.

U.S. Pat. No. 3,092,555 to Horn is directed to relatively collapsible foam products intended to be delivered from an aerosol container. Although some very general statements are made by Horn as to using his concept to deliver pharmaceuticals, lubricants, and shampoos, his teachings are particularly directed to providing products wherein hair coloring dyes are dissolved or dispersed in the foamable liquid of his invention. There is no suggestion for suspending reflective particulate material in the Horn composition to provide a means for applying temporary "glitter" to hair.

The British patent to Steiner 721,045 published Dec. 29, 1954 relates to process and device for tinting or coloring hair. In his invention, Steiner employs colors in the form of particles of pigment, metallic powders or "other finely divided powders". In accordance with the Horn disclosure, particles coated with fixatives are sprayed onto hair. In the alternative, the colored particles first sprayed onto the hair are followed by a spray of fixative. The use of the moderately fast-breaking foam of the present invention is not shown in Steiner.

The primary vehicle for the foamable liquid composition of the present invention will usually be water. In an alternative form of this invention, a water miscible, cosmetically acceptable volatile solvent can also comprise a part of the primary vehicle. Suitable solvents of this kind include lower fatty alcohols e.g. ethyl alcohol, n-propyl alcohol, isopropyl alcohol.

The quantity of primary vehicle that will comprise the foamable liquid of this invention can vary somewhat. Generally, this will constitute from about 50% to about 95% by weight based on the total weight of the foamable composition with the preferred ranges being from about 60% to about 94% on the same weight basis. When a volatile solvent is employed along with the water in constituting the primary vehicle, again the relative quantities of the respective material can vary over a range. Usually, this ratio, on a weight basis, will be from about 50:35 to 65:25.

As reflective particles that can be advantageously used this invention any of a wide variety of materials can be employed. These include such materials as metallic or non-metallic micas, bismuth oxychloride. Organic materials such as guanines (fish scales), etc. can also be utilized. The particle size of these particles is not especially critical. They should, however, be of a suitable size so that they can properly reflect light and give an esthetic appearance when deposited on the hair. Generally, however, this particle size will fall within the range of from about 1 to 60 micons.

The reflective particles will be suspended in this foamable liquid composition in an amount sufficient to give the hair the desired high fashion look when the composition is deposited on the hair as a foam and spread over its surface. For the most part, these particles will constitute from about 1% to about 10% by weight based on the total weight of the foamable liquid of which they are a part. Optimal results are obtained when this level is in the range of from about 2% to about 4% on the same weight basis.

A further essential ingredient of the foamable liquid embodied in this invention which will provide a moderately fast breaking foam when dispensed from an aerosol can is the foaming agent. This will usually take the form of a surfactant of the anionic, non-ionic or amphoteric type. These can be employed singly or in combination with each other. That is to say that, mixtures of surfactants of the same type or of different types can be employed. By way of illustrating the useful surfactants for the present purposes, the following can be mentioned: fatty alcohols, fatty acid alkanolamides of the superamide type where the fatty portion can be from $C_8$-$C_{18}$; polyethylene glycol ether fatty alcohols ranging from 8 moles to 45 moles in ethoxylation; polyethylene, polyoxypropylene block polymers (preferably with a minimum of 30% ethoxylation in the total molecule and a range of molecular weight for the polyoxypropylene hydrophobe from 950–4000); sodium-, ammonium-, triethanolamine lauryl sulfate; sodium lauryl ether sulfate; sodium or -olefin sulfonate; sodium lauroyl sarcosinate; sodium cocoyl isothionate; dioctyl sodium sulfosuccinate.

Quite unexpectedly, experimentation has shown that the combination of cetyl alcohol and ethanol acts in a manner to inhibit caking of the colorants; yet provides a rich foam. This is not the case with traditional anionic foaming agents (as in the Horn patent) where severe caking of the colorants occurs on standing.

The effective amount of foaming agent that will be used can vary. All that is essential is that enough of this agent by employed to provide a moderately fast-breaking foam when the product is dispensed from the aerosol can. Usually, this will amount to from about 0.1% to about 2.0% by weight based on the total weight of the composition, with the preferred range being from about 0.2% to about 1.0% on the same weight basis.

It is highly advantageous to also include in the foamable composition of this invention a water-soluble hair setting resin or resins. These have the virtues of serving as styling aids or hair conditioners as well as a fixative to retain the reflective particles on the hair. The quantity of this resin or resins that can be incorporated in the present foamable compositions can vary depending on the resin or resins selected and the results desired. Usually, this resin component will constitute between about 0.5% to about 10% by weight based on the total weight of the composition, with the preferred range being from about 1% to about 4% on the same weight basis.

The resin or resins best suited for the purposes of this invention are the synthetic resins and particularly, vinylic resins. Examples of such resin include conditioning and/or hair setting agents given below that can be employed alone or in combination with each other: vinyl pyrrolidone/dimethylamino-ethylmethacrylate copolymers; polyvinyl pyrrolidone; methacryloyl ethyl betaine/methacrylate copolymer; vinyl caprolactam vinyl pyrrolidone/vinyl pyrrolidone/dimethylaminoethylmethylacrylate copolymer; half esters of vinylmethyl ether/maleic anhydride copolymers; water soluble quaternary cellulose copolymers chiefly of the hydroxyethylcellulose/diallyldimethyl ammonium chloride type.

It is also sometimes advantageous to be able to impart a color to the reflective particles employed in this invention. With this in mind, water insoluble pigments can be incorporated in the present foamable liquid. Suitable pigments include ferric ferrocyanide, iron oxides, etc. When present, these pigments will be included in the foamable liquid at a level of from about 0.5% to about 20% by weight based on the total weight of the foamable liquid, the preferred level being from about 1% to about 5% on the same weight basis.

The foamable compositions can also contain auxiliary hair conditioning agents. These can be employed to improve the texture or feel of the hair. A number of hair conditioning agents known in the prior art would serve this purpose. These include such things as dimethylpolysiloxane, dimethylsiloxane-glycol copolymers. These auxiliary hair conditioners, when employed, will be utilized at a concentration in the range of from about 0.5% to about 5% by weight based on the total weight of the foamable composition, and optimally, at a level in the range of from about 1% to about 3% on the same weight basis.

Foamable liquid of the present invention is intended to be packaged in an aerosol can under pressure for dispensing a moderately fast-breaking foam. There will, accordingly, also be incorporated in the aerosol container a propellant system which will be part of the foamable liquid. Any of a number of propellants known in this art, which are compatible with the composition, can be employed herein. These include hydrocarbons, fluorocarbons, ethers, etc. Examples of such propellants include Hydrofluorocarbon 152a (1,1-difluoroethane) hydrofluoro carbon-22, isobutane, isopropane dimethy ether used alone or in combination. A preferred propellant system is a blend of Hydrofluorocarbon 152a and isobutane wherein the ratio of the Hydrofluorocarbon 152a to isobutane is in the range of from about 80:20 to 60:40.

The amount of propellant system that will be contained in the present foamable composition will ordinarily be in the range of from about 3% to about 20% by weight based on the total weight of the foamable composition. Optimally, this concentration will be in the range of from about 3% to about 15% on the same weight basis.

The procedure for preparing the products of this invention and the mode for applying them are as follows:

Procedure

Dissolve water-soluble ingredients in water phase and alcohol soluble ingredients in the alcohol e.g. ethanol. Add ethanol phase to water phase. Load this concentrate in an aerosol can and use foam aerosol valve load propellants.

Direction for Use

Shake can well before use. Apply foam on wet or dry hair and set as required or blow dry.

The following Examples are given to further illustrate this invention. It is to be understood, however, that the invention is not limited thereto.

| Type A Formula | Wt. % | | |
|---|---|---|---|
| Ingredient | A-1 | A-2 | A-3 |
| Polyquaternium11 | 5.0 | 8.0 | 12.0 |
| Isosteareth-10 | — | 0.1 | 0.2 |
| Sodium Cocoyl Isothionate | .05 | 0.2 | 0.1 |
| Dimethicone Copolyol | .10 | — | .05 |
| Lauramide DEA | .30 | .30 | .40 |
| Fragrance | .10 | .10 | .10 |
| DMDM Hydantoin | .20 | .20 | .20 |
| Methylparaben | .10 | .10 | .10 |
| Mica and Titanium Dioxide | 2.0 | 2.0 | 5.0 |
| Iron Oxides | — | 1.0 | — |
| Propellant Blend | 6.0 | 10.0 | 15.0 |
| D.I. Water | Bal. | Bal. | Bal. |
| | 100.0 | 100.0 | 100.0 |

| Type B Formula | Wt. % | | |
| --- | --- | --- | --- |
| Ingredient | B-1 | B-2 | B-3 |
| Polyquaternium-4 | 1.0 | 3.0 | 5.0 |
| Quaternium-26 | — | .5 | 1.0 |
| Ceraphyl-85* | 1.0 | .5 | — |
| Cetyl Alcohol | .3 | .2 | .1 |
| SDA 40- | 10.0 | 20.0 | 30.0 |
| Fragrance | .1 | .1 | .1 |
| Mica and Titanium Dioxide | 2.0 | 2.0 | 5.0 |
| Iron Oxide | — | 1.0 | — |
| Propellant | 6.0 | 10.0 | 15.0 |
| D.I. Water | Bal. | Bal. | Bal. |
| | 100.0 | 100.0 | 100.0 |

| Type C Formula | Wt. % | | |
| --- | --- | --- | --- |
| Ingredient | C-1 | C-2 | C-3 |
| Celquat 200 (National Search) | 2.0 | 5.0 | 8.0 |
| Gafquat 755N (GAF) | 16.0 | 8.0 | 4.0 |
| Siponic E-5 (Alcolac) | 1.0 | 20.0 | 30.0 |
| Anhydrous Ethyl Alcohol SD-40 | 10.0 | 20.0 | 30.0 |
| Fragrance | .1 | .1 | .1 |
| Mica and Titanium Dioxide | 2.0 | — | — |
| Iron Oxide | 1.0 | — | 1.0 |
| Bismuth Oxychloride | — | 4.0 | — |
| Guanines (fish scale) | — | — | 4.0 |
| Propellant | 6.0 | 10.0 | 15.0 |
| Water | Bal. | Bal. | Bal. |
| | 100.0 | 100.0 | 100.0 |

| Type D Formula | Wt. % | | |
| --- | --- | --- | --- |
| Ingredient | D-1 | D-2 | D-3 |
| Distilled Water | Bal. | Bal. | Bal. |
| Polyquaternium-11 | 4.0 | 7.0 | 10.0 |
| PVP/VA Copolymer | 3.0 | 2.0 | 1.0 |
| Oleth-20 | 0.4 | .5 | .4 |
| SDA-40 | 10.0 | 15.0 | 20.0 |
| Methylparaben | .1 | .1 | .1 |
| Fragrance | .1 | .1 | .1 |
| Mica and Titanium Dioxide | 2.0 | 4.0 | 6.0 |
| Iron Oxide | 2.0 | 1.0 | — |
| Propellant | 6.0 | 10.0 | 15.0 |
| Distilled Water | Bal. | Bal. | Bal. |
| | 100.0 | 100.0 | 100.0 |

| Ingredient Concentrate | % by Weight | | | |
| --- | --- | --- | --- | --- |
| | E-1 | E-2 | E-3 | E-4 |
| Polyquaternium-4 | 1.00 | → | → | → |
| Quaternium-26 | 0.75 | → | → | → |
| *Stearamidopropyl Cetearyl Dimonium Tosylate & Propylene Glycol | 0.50 | → | → | → |
| Cetyl alcohol | 0.50 | → | → | → |
| SDA 40-200* | 27.73 | → | → | → |
| Fragrance FS-660 | 0.20 | → | → | → |
| Mica | 2.4 | 2.2 | 2.6 | 2.12 |
| Titanium oxide | 1.4 | 1.64 | .12 | .08 |
| Iron oxide | .2 | .16 | 1.28 | 1.8 |
| D.I. Water Q.S. | 100 | → | → | → |

*Ceraphyl 85

92% by weight of each of the above described concentrates E-1 through E-4 were placed in an aerosol can and then blended with 8% by weight of propellant. The propellant was a mixture of Hydrofluorocarbon 152A ($CH_3CHF_2$) 75% and isobutane 25%.

We claim:

1. A composition for depositing reflective particles on hair which composition consists essentially of from about 0.5 to about 20% pigment and from about 1 to about 10% by weight, based on total weight of foamable liquid, dispersed in a foamable liquid, wherein the liquid contains:
   (a) a sufficient quantity of an aqueous solution of a water soluble resin to serve as a styling aid and fixative for the particles; and
   (b) from 1 to 2% a foaming agent consisting essentially of cetyl alcohol ethanol and water, said foaming agent being present in an amount sufficient to inhibit caking and to provide a moderately fast-breaking foam when the product is dispersed from an aerosol can.

2. The composition of claim 1 wherein the reflective particles comprise about 1 to about 10% by weight, the resin comprises about 0.5 to about 10% by weight, and the foaming agent comprises about 0.1 to about 2.0% by weight, based on total composition weight.

3. The composition of claim 1 further containing a water insoluble pigment dispersed therein.

4. The composition of claim 3 in which the reflective particles are mica particles.

5. A fast-breaking foam produced by activating a foamable composition consisting essentially of reflective particles, a colorant, a propellant, a sufficient quantity of an aqueous resin solution to serve as a styling aid and fixative for the particles and, as foaming agent, a combination of cetyl alcohol ethanol and water, wherein the combination is present in an amount sufficient to inhibit caking and to provide a moderately fast-breaking foam when the product is dispersed from an aerosol can.

6. The foam of claim 5 wherein the foaming agent makes up for about 0.1 to about 2.0 weight % of the composition.

7. A method of inhibiting the caking of a colorant in an aqueous foam composition which method comprises the step of incorporating an anticaking amount of the combination of cetyl alcohol and ethanol therein, wherein the combination is present in an amount which provides a moderately fast-breaking foam when the product is dispersed from an aerosol can.

8. An aerosol container containing a foamable liquid composition under pressure, said liquid containing:
   (a) from about 1 to about 10% by weight, based on the weight of the foamable liquid of reflective particles;
   (b) from about 0.5 to about 20% by weight, based on the weight of the foamable liquid, of a pigment as a colorant; and
   (c) a foaming agent consisting essentially of cetyl alcohol ethanol and water, present in an amount sufficient to inhibit caking and to provide a moderately fast-breaking foam when the product is dispersed from an aerosol can.

9. The container of claim 8 wherein the foaming agent comprised from about 0.1 to about 2% by weight of the total weight of the composition in the container.

10. The container of claim 8 which also contains an aerosol propellant.

11. The container of claim 10 wherein the reflective particles are mica particles.

* * * * *